United States Patent [19]
Palti

[11] Patent Number: 4,583,979
[45] Date of Patent: Apr. 22, 1986

[54] INFUSION DEVICES

[76] Inventor: Yoram Palti, 51 Ruth Street, Haifa, Israel

[21] Appl. No.: 582,718

[22] Filed: Feb. 23, 1984

[30] Foreign Application Priority Data

Dec. 14, 1983 [IL] Israel .......................... 70447

[51] Int. Cl.⁴ .............................................. A61M 5/00
[52] U.S. Cl. ...................................... 604/256; 604/251; 604/283; 604/905
[58] Field of Search ................ 604/251, 256, 905, 283

[56] References Cited

U.S. PATENT DOCUMENTS

| | | | |
|---|---|---|---|
| 3,800,799 | 4/1974 | McWhorter | 604/256 |
| 3,835,862 | 9/1974 | Villari | 604/256 |
| 4,294,247 | 10/1981 | Carter et al. | 604/95 |
| 4,405,163 | 9/1983 | Voges et al. | 604/283 |
| 4,473,369 | 9/1984 | Lueders et al. | 604/283 |

Primary Examiner—R. L. Andrews
Attorney, Agent, or Firm—Fleit, Jacobson, Cohn & Price

[57] ABSTRACT

There is provided a drop counting chamber for use in infusion devices which provides a hermetic closure between the infusion liquid and the syringe needle when in storage, and which can easily be actuated. The device prevents entrance of any air bubbles into the infusion liquid.

9 Claims, 11 Drawing Figures

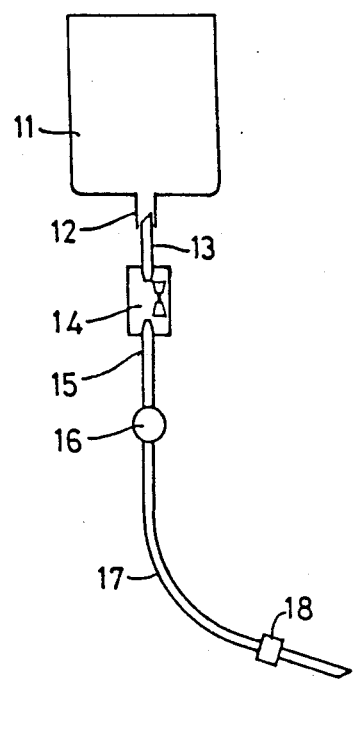
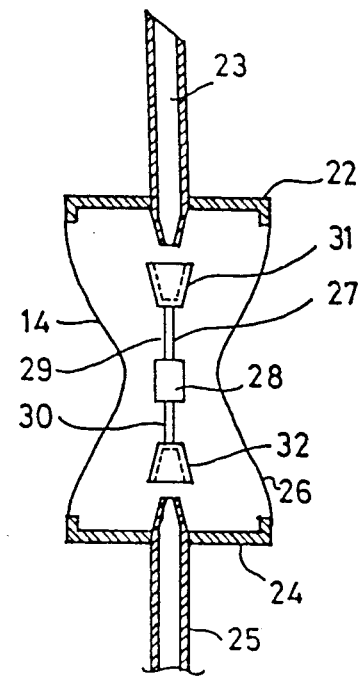
FIG. 1                FIG. 2
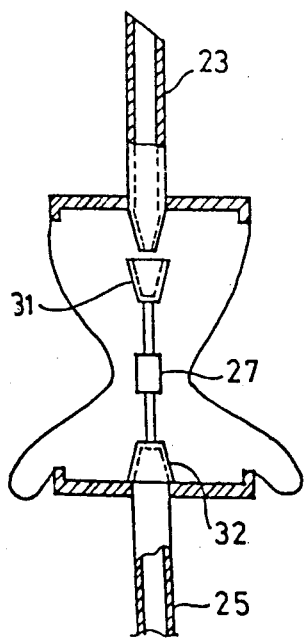
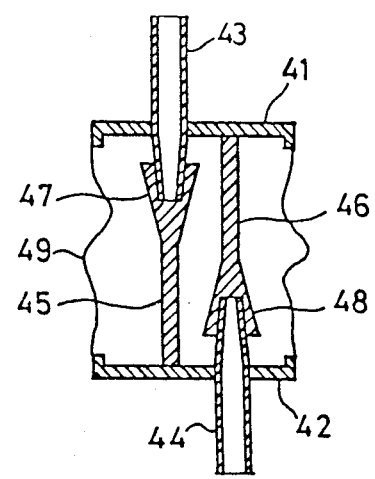
FIG. 3                FIG. 4

4,583,979

INFUSION DEVICES

FIELD OF THE INVENTION

The invention relates to improvements in devices for use in infusion setups. The device of the invention is a disposable one, it is adapted to be connected on the one hand with the container of the liquid to be administered, and on the other, via a hypodermic needle or catheter to the patient. The penetration of air bubbles is obviated and the infusion can be rapidly commenced without further preparations.

BACKGROUND OF THE INVENTION

There are known many types of infusion devices. Infusions are either applied by gravitational feed or under a certain pressure. Many types of automated systems are known. It is one of the main problems of infusion devices that the introduction of air bubbles into the blood stream is highly dangerous and must be prevented. To this end various devices and techniques have been provided. According to the present invention, a very simple and inexpensive device and technique is provided with which the infusion can be initiated rapidly, and in a safe and simple manner, at the same time preventing the introduction of air bubbles with the infusion, there being provided the conventional means for visually monitoring the rate of the infusion.

SUMMARY OF THE INVENTION

According to the invention there is provided a device for use with infusion appliances. The novel device is connected by tubing to the container of the liquid which is to be infused, and on its other end via a hypodermic needle to the vein of the patient. Compared with this, the actuation of the application of an infusion by means of the novel device is simple and rapid; it comprises removing the protective sterile wrapping, hanging the container, breaking the liquid seals, removal of needle protecting means, insertion of needle into vein and opening and adjusting the flow valve. It is also possible to preset the flow regulating valve for a predetermined rate with a certain type of liquid. When the set according to the invention is supplied separate from the liquid container, the further step of introduction of the spike of the set into the liquid container is required.

The danger of penetration of air into the vein with the solution applied during the infusion is a very serious one. There exist a variety of sources of such air:

a. air is present in the infusion bag (liquid container) which is not completely filled with liquid;

b. the drop counting chamber must be only partially filled with liquid, and air must be present above the liquid level;

generally air is initially present in the tubings. However even if these are prefilled with liquid, as air dissolves in such liquids and depending on the temperature, the solubility of such air or other gases varies: if at the time of use or of storage of the prefilled tubing the temperature is higher than that at the time the set was filled with liquid, air bubbles will form in the solution, and may be infused to the patient.

The inherent dangers of introduction of air during infusion are obviated by the device of the invention.

The device according to the invention can be supplied separately, to be connected with a container of the solution to be infused, or it can be supplied as integral part of a complete infusion set, with such container and liquid. In the following, the device of the invention will be illustrated according to the embodiment which is to be connected via a spike with the liquid container prior to the actuation of the infusion. The device of the invention consists essentially of two rigid disks attached to a flexible transparent or translucent sleeve so as to form a cylindric container, inlet and outlet tubes being provided respectively at each end of the disks. At the interior of the cylindrical member removable means are provided for closing the two openings of the said tubings at the interior of sid container; said closures being removable at will. The internal closing means can be interconnected so as to form an entity, which is shorter than the distance between the two openings of the outlet tubes when the flexible cylindrical member is fully extended. The two ends of such closure member can be of conical shape, to fit the parts of the two tubes. There can also be provided cup-shaped closures for each of the two outlets, and these can be attached to the opposite disks. According to another embodiment of the invention, the middle of the closure member is attached by a flexible cord or the like to the two disks. The main idea is to provide for the hermetic sealing of the two openings of the tubes in the device up to the time when the device is to be actuated, and the possibility to open these, for a free liquid flow, by simple means when the infusion is to be started. The closing means of the two ends of the tubes extending into the drop counting chamber prevent the introduction of air bubbles into the infusion liquid from said chamber into the tubing leading to the hypodermic needle.

BRIEF DESCRIPTION OF THE DRAWINGS

The invention is illustrated with reference to the enclosed schematical drawings, which are not according to scale and in which:

FIG. 1 is a perspective view of an infusion device;

FIG. 2 is a sectional view through a device of the invention;

FIG. 3 is a view of the device of FIG. 2 with closure member attached to one of the outlets;

FIGS. 4 and 5 are sectional side views of a different embodiment of the device;

DETAILED DESCRIPTION OF THE DRAWINGS

Figure 5:
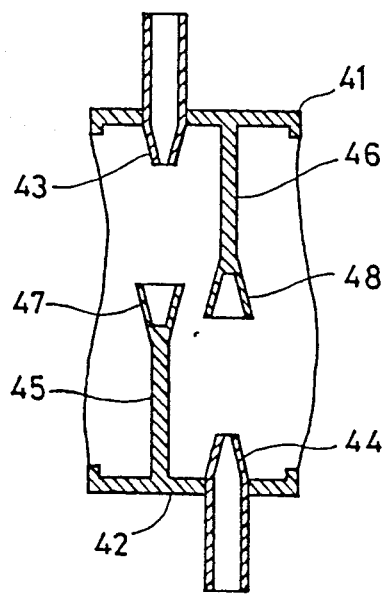
Figure 6:
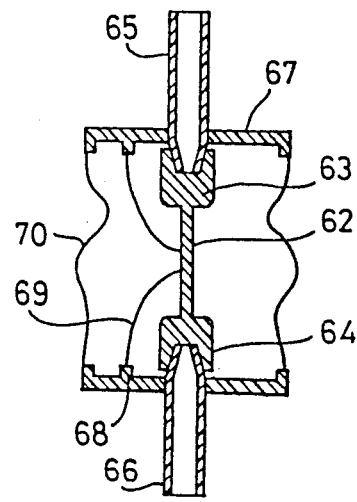
FIGS. 6 and 7 illustrate another embodiment of the invention by sectional side views.
Figure 7:
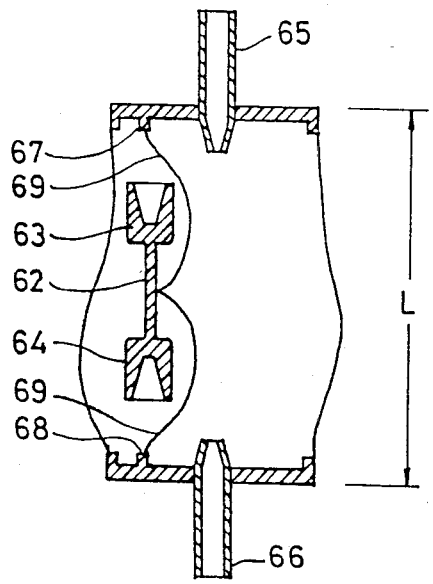
Figure 8:
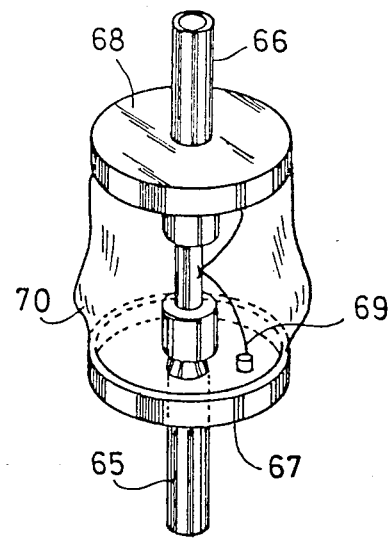
FIGS. 8 and 9 are perspective views of devices of FIGS. 6 and 7.
Figure 9:
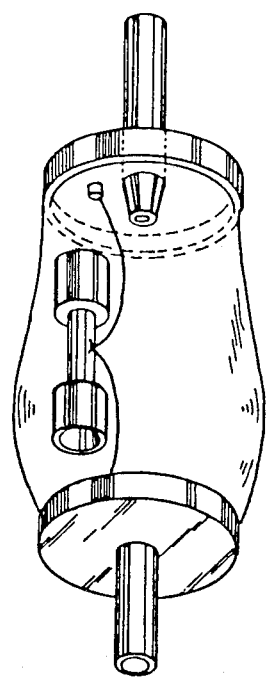

As shown in FIG. 1, an infusion device comprises in combination a liquid storage vessel or container 11, made generally of a resilient plastic, with outlet tube 12, connected via spout 13 to the drop counting chamber 14 which is provided with an outlet tube 15, which is provided with a valve 16 to tubing 17, to hypodermic needle 18.

As shown in FIGS. 2 and 3, the chamber of the device of the invention 14 which replaces the conventional drop counting chamber, is replaced by a chamber which consists of an upper circular disk 22 of about 2 to 3 cm diameter, provided with a central inlet tube 23, a similar lower disk 24 provided with outlet tube 25, and a circumferential plastic resilient cylindrical sleeve 26, there being provided a rod-shaped member 27 comprising a central part 28 from which there extend rods 29 and 30, provided at their ends with cup-shaped structures 31 and 32 respectively, adapted to be attached simultaneously to close the openings of tubes 23 and 25, the attachment to the lower tube 25 being illustrated with reference to FIG. 3. When the said central member 27 is attached to the two tubes, the plastic sleeve bends over.

When it is desired to actuate the device, the upper tube 23 or spike is attached to the liquid container, while the lower tube extends to the hypodermic needle as shown in FIG. 1. At this stage the hypodermic needle is inserted into the vein of the patient and the central part 28 is gripped through the plastic with the fingers and the closures are pulled off from the inlet and outlet tubes so as to be in the position shown in FIG. 2.

As shown in FIGS. 4 and 5 the device comprises circular disks 41 and 42, provided respectively with inlet andoutlet tubes 43 and 44, respectively, there being attached to, and forming an integral part with said disks 41 and 42 rod-shaped members 45 and 46, which have at their ends cup-shaped members 47 and 48 adapted to simultaneously close the outlets of the tubes 43 and 44, there being provided a transparent plastic circumferential sleeve 49. When the infusion is to be actuated, the sleeve, which is of a greater height than the combined length of the tubes and their counterparts, is pulled apart by pulling on the disks so as to remove the closures and open the device for the liquid flow.

A similar device is illustrated in FIG. 6 to 9 where the internal closure member 61 comprises a rod 62 provided at both its ends with cup-shaped members 63 and 64 adapted to engage the outlets of inlet and outlets tubes 65 and 66, the central part of the rod 62 being attached to the disk 67 and to the disk 68 by a string 69, the sleeve 70 being in an outwardly or inwardly protruding position when said closures are applied to the inlet and outlet tubes. When the device is to be actuated, the disks are gripped and pulled apart to extend the sleeve to its full height, thus pulling off the cup-shaped closures from the tubes, opening the flow of liquid.

Figure 10:
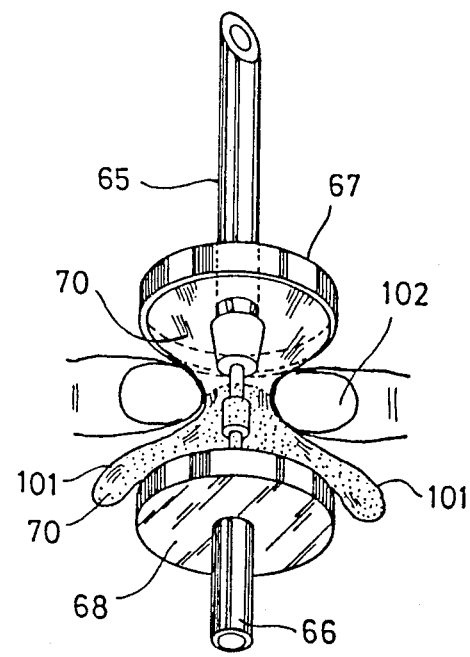
FIGS. 10 and 11 are perspective side views of another embodiment of the invention.
Figure 11:
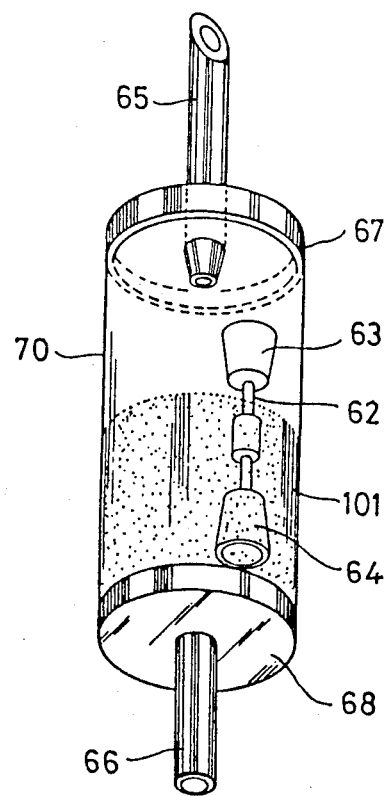

A device similar to that of FIG. 2 is illustrated in FIG. 10, which illustrates the provision of a liquid 101 in the device, which is supplied with the tubing leading to the hypodermic needle being filled with a degassed liquid (generally a physiological solution). When it is desired to actuate the device, the central part is gripped by the fingers 102 shown in the Figure and the device is fully extended to the position illustrated in FIG. 11.

Preferably the device is provided with a quantity of physiological solution to fill the drop counting chamber to about half its height, and with a degassed liquid filling the tubing, the valve and hypodermic needle to its exit which is provided with closing means which maintains sterility and prevents the internal fluid from flowing outwards, adapted to be removed before use.

As stated above, the disks are generally of about 20 to 30 mm diameter, the height of the extended device is ablout 50 mm to 80 mm. The sleeve can be provided with a protruding central part which facilitates the bending of same when the device is in the storage position with internal closures in position.

The device is advantageously supplied partially filled with a suitable liquid.

Furthermore, there can be supplied an integrated device which comprises a component as defined above, in combination with a container containing the infusion liquid, and with a conduit ending in a hypodermic needle or catheter which are provided with protective means until the infusion is initiated.

It is clear that the above description is by way of illustration only and that various modifications and changes in the structure and arrangement of parts can be resorted to without departing from the invention.

I claim:

1. A drop-counting chamber for use in an infusion device, comprising a transparent or translucent resilient tubular sleeve having two ends and closed at each end by a hermetically bonded disk, inlet means connected to one of said disks and outlet means connected to the other of said disks, each of said inlet and outlet means having a fluid port member extending into the drop-counting chamber, said port members being located opposite one another and removable closure means within said chamber and engagable with said port members to close or open said port members, said closure means capable of simultaneously closing both of said port members.

2. A drop-counting chamber as claimed in claim 1 wherein said port members are tapered.

3. A drop-counting chamber as claimed in claim 2, wherein the closure means provided in said chamber comprises a rod-shaped elongated part terminating at its two ends in cup shaped members adapted to close said tapered port members, the arrangement of said closure means and port members being such that the port members are closed by said closure means while the sleeve is not in a fully extended position, and the opening of said port members being effected by manual means, whereby the sleeve is fully extended to its cylindrical shape.

4. A drop-counting chamber as claimed in claim 1, wherein the two disks are circular in shape, the sleeve is made from transparent thin plastic sheeting, and said port members of the tubes are coaxially located and face each other.

5. A drop-counting chamber according to claim 2, wherein the rod is attached to the disks by a string, so that when the disks are pulled apart to the full height of the sleeve, said closure means are removed from the said tapered members.

6. A drop-counting chamber according to claim 1, wherein said port members are displaced from the center of the disk, and where opposite each of said port members there is provided a rod-shaped member terminating in a cup-shaped member, so that both port members can be closed by said cup-shaped members by being attached to them when the plastic sleeve is not fully extended.

7. A drop-counting chamber according to claim 1, wherein said closures are removable at will before actuation of the infusion.

8. A drop-counting chamber according to claim 1, wherein said outlet means is attached to an exit tube which is attached to a valve and to a hypodermic needle, said tubing and needle being filled with a degassed physiologically acceptable solution.

9. An infusion device comprising a drop-counting chamber as claimed in claim 1, forming an integral entity with a container of the infusion liquid attached thereto at its upper end, and a tubing ending at a hypodermic needle at its lower end, said drop-counting chamber being supplied half filled with a degassed liquid, which fills also the tubing up to the end including the hypodermic needle.

* * * * *